United States Patent
Wang et al.

(10) Patent No.: US 10,472,788 B2
(45) Date of Patent: Nov. 12, 2019

(54) DEVICES USED IN LABORATORIES TO MEASURE HORIZONTAL DISPLACEMENT OF SOIL AROUND A FOUNDATION TO BE TREATED BY VACUUM PRELOADING, AND MEASUREMENT METHODS

(71) Applicant: WENZHOU UNIVERSITY, Wenzhou, Zhejiang Province (CN)

(72) Inventors: Jun Wang, Wenzhou (CN); Yuanqiang Cai, Wenzhou (CN); Hongtao Fu, Wenzhou (CN); Changxin Shi, Wenzhou (CN); Peng Wang, Wenzhou (CN); Junfeng Ni, Wenzhou (CN); Ziquan Fang, Wenzhou (CN)

(73) Assignee: WENZHOU UNIVERSITY, Wenzhou (CN)

( * ) Notice: Subject to any disclaimer, the term of this patent is extended or adjusted under 35 U.S.C. 154(b) by 113 days.

(21) Appl. No.: 15/712,689

(22) Filed: Sep. 22, 2017

(65) Prior Publication Data
US 2018/0282966 A1    Oct. 4, 2018

(30) Foreign Application Priority Data
Mar. 30, 2017    (CN) .......................... 2017 1 0200805

(51) Int. Cl.
*E02D 3/10* (2006.01)
*G01N 33/24* (2006.01)

(52) U.S. Cl.
CPC ........ *E02D 3/10* (2013.01); *E02D 2250/0053* (2013.01); *E02D 2600/10* (2013.01); *E02D 2600/20* (2013.01); *G01N 33/24* (2013.01)

(58) Field of Classification Search
CPC ...... G01N 33/24; G01N 33/246; G01N 15/08; G01N 15/0826; G01N 13/02
See application file for complete search history.

(56) References Cited

U.S. PATENT DOCUMENTS 2,141,261 A * 12/1938 Baldwin ................ G01V 9/007
166/264
4,065,972 A * 1/1978 Holub .................... G01V 9/007
436/29

(Continued)

FOREIGN PATENT DOCUMENTS

| CN | 105929132 A | * | 9/2016 | ............... E02D 3/10 |
| CN | 108824502 A | * | 11/2018 | ............. E02D 33/00 |

*Primary Examiner* — David A Rogers
(74) *Attorney, Agent, or Firm* — Jiwen Chen

(57) ABSTRACT

A laboratory device to measure horizontal displacement of soil around a region treated by vacuum preloading includes a box injected with dredger fill. A vertical drainage board and a vacuum pumping tube are buried within soil in the treatment region in connection with a vacuum degree detector and a vacuum pump. A seal membrane covers soil in the treatment region. A loading device is above the seal membrane. Transverse tubes are inserted into a side of the box and in surrounding soil of the treatment region. An annular sensing source, which moves together with the soil and which is movable along the transverse tubes, sleeved on the transverse tubes. Each transverse tube is provided with a sensing instrument, and the sensing instrument is connected with a sensor is inserted into the transverse tube. The different positions of the sensing source at different moments of time are determined.

10 Claims, 2 Drawing Sheets

(56) References Cited

U.S. PATENT DOCUMENTS

| | | | | |
|---|---|---|---|---|
| 4,068,525 A | * | 1/1978 | Skaling | G01N 7/10 73/73 |
| 4,137,931 A | * | 2/1979 | Hasenbeck | A01G 25/167 137/78.3 |
| 4,164,139 A | * | 8/1979 | Jones | G01N 33/42 73/38 |
| 4,332,172 A | * | 6/1982 | Torstensson | E21B 47/06 73/700 |
| 4,885,941 A | * | 12/1989 | Vardoulakis | G01N 3/08 73/794 |
| 4,922,945 A | * | 5/1990 | Browne | A01G 25/167 137/624.11 |
| 4,969,111 A | * | 11/1990 | Merva | E21B 49/008 324/694 |
| 5,000,051 A | * | 3/1991 | Bredemeier | E21B 7/26 73/73 |
| 5,161,407 A | * | 11/1992 | Ankeny | G01N 15/0893 73/38 |
| 5,179,347 A | * | 1/1993 | Hawkins | G01N 27/121 324/694 |
| 5,345,820 A | * | 9/1994 | Bernhardt | E21B 49/008 73/152.18 |
| 5,548,991 A | * | 8/1996 | Ritson | G01N 15/0826 175/21 |
| 5,857,289 A | * | 1/1999 | Franco da Encarnacao | A01G 27/008 47/79 |
| 5,941,121 A | * | 8/1999 | Faybishenko | E21B 47/06 73/73 |
| 6,236,941 B1 | * | 5/2001 | Kram | G01N 33/24 702/12 |
| 6,263,726 B1 | * | 7/2001 | Hubbell | G01N 7/10 73/152.05 |
| 6,938,461 B1 | * | 9/2005 | Johnson | E21B 49/00 73/37 |
| 6,976,386 B1 | * | 12/2005 | Grover | E21B 49/08 137/78.2 |
| 8,650,948 B2 | * | 2/2014 | Lee | G01F 1/00 702/45 |
| 8,714,034 B2 | * | 5/2014 | Zimbron | B01D 53/0415 73/863 |
| 9,371,729 B2 | * | 6/2016 | Brown | G01N 33/24 |
| 9,377,392 B2 | * | 6/2016 | Rickards | G01N 19/00 |
| 9,546,940 B2 | * | 1/2017 | Gupta | G01N 3/08 |
| 9,822,504 B2 | * | 11/2017 | Puppala | E02D 1/022 |

* cited by examiner

DEVICES USED IN LABORATORIES TO MEASURE HORIZONTAL DISPLACEMENT OF SOIL AROUND A FOUNDATION TO BE TREATED BY VACUUM PRELOADING, AND MEASUREMENT METHODS

This application claims the priority benefit of Chinese Application No. 201710200805.4 filed Mar. 30, 2017, which is hereby incorporated by reference.

TECHNICAL FIELD OF THE INVENTION

The present invention relates to a device, used in indoor tests where a foundation is to be treated by vacuum preloading, to measure horizontal displacement of soil around a region to be treated. The present invention also relates to a method, used in indoor tests where a foundation is to be treated by vacuum preloading, to measure horizontal displacement of soil around a region to be treated.

BACKGROUND OF THE INVENTION

The foundation treatment by vacuum preloading has a great influence on the surrounding soil, especially the horizontal displacement of the surrounding soil, which may cause great harm. However, at present, during the simulation of foundation treatment in laboratories by vacuum preloading, there is no device that can measure the amount of horizontal displacement of soil around the region to be treated.

SUMMARY OF THE INVENTION

In view of the deficiencies in the prior art, a technical problem to be solved in the present invention is to provide a device which can accurately measure the amount of horizontal displacement of soil around the foundation when treated by vacuum preloading in indoor tests. The present invention also relates to a method which can measure the amount of horizontal displacement of soil around the foundation when treated by vacuum preloading in indoor tests.

For those purposes, the present invention provides a device used in laboratories to measure horizontal displacement of soil around a region to be treated by vacuum preloading, including a box; dredger fill is injected into the box; a vertical drainage board and a vacuum pumping tube are buried within soil in the region to be treated, with the vacuum pumping tube being provided with a vacuum degree detector, a lower end of the vacuum pumping tube being connected to the plastic drainage board and an upper end thereof being connected to a vacuum pump, and a seal membrane covering or wrapping soil in the region to be treated so that the interior of the seal membrane is kept sealed; a loading device is provided above the seal membrane to assist the drainage; transverse tubes are inserted into a side of the box, the transverse tubes being in surrounding soil of the region to be treated; an annular sensing source which is movable along the transverse tubes together with soil is sleeved on the transverse tubes; each of the transverse tubes is provided with a sensing instrument, and the sensing instrument is connected with a sensor which can be inserted into the transverse tube; when the sensor reaches the sensing source, an alarm signal is sent, and in this way, the different positions of the sensing source at different moments of time are determined.

The present invention further provides a method for measuring horizontal displacement of soil around a region to be treated by vacuum preloading, by using the device used in laboratories to measure horizontal displacement of soil around a region to be treated by vacuum preloading, comprising the following steps:

A: injecting dredger fill into a box of the device for measuring horizontal displacement of soil around a region to be treated by vacuum preloading; burying a vertical drainage board and a vacuum pumping tube within soil in the region to be treated, with the vacuum pumping tube being provided with a vacuum degree detector, a lower end of the vacuum pumping tube being connected to the plastic drainage board and an upper end thereof being connected to a vacuum pump, and a seal membrane covering or wrapping soil in the region to be treated so that the interior of the seal membrane is kept sealed; then activating the vacuum pump so that a negative pressure is formed below the seal membrane; and loading above the seal membrane by using the loading device to form a positive pressure;

B: inserting the sensor into the transverse tubes at regular intervals and recording the sensed position of the annular sensing source; and C: calculating the amount of displacement of the annular sensing source according to the data of the position of the annular sensing source sensed by the sensor, detecting and obtaining the vacuum degree data by using a vacuum degree detector, calculating and loading the data by the loading device, and establishing a test model together with the amount of displacement, the loading force data, the vacuum degree data and the time span.

The present invention has the beneficial effects that the amount of horizontal displacement of soil around the region to be treated by vacuum preloading can be quickly measured; and that the measured data is accurate, the operation is simple, and the whole test device is simple in structure and low in cost.

DETAILED DESCRIPTION OF THE INVENTION

Figure 1:
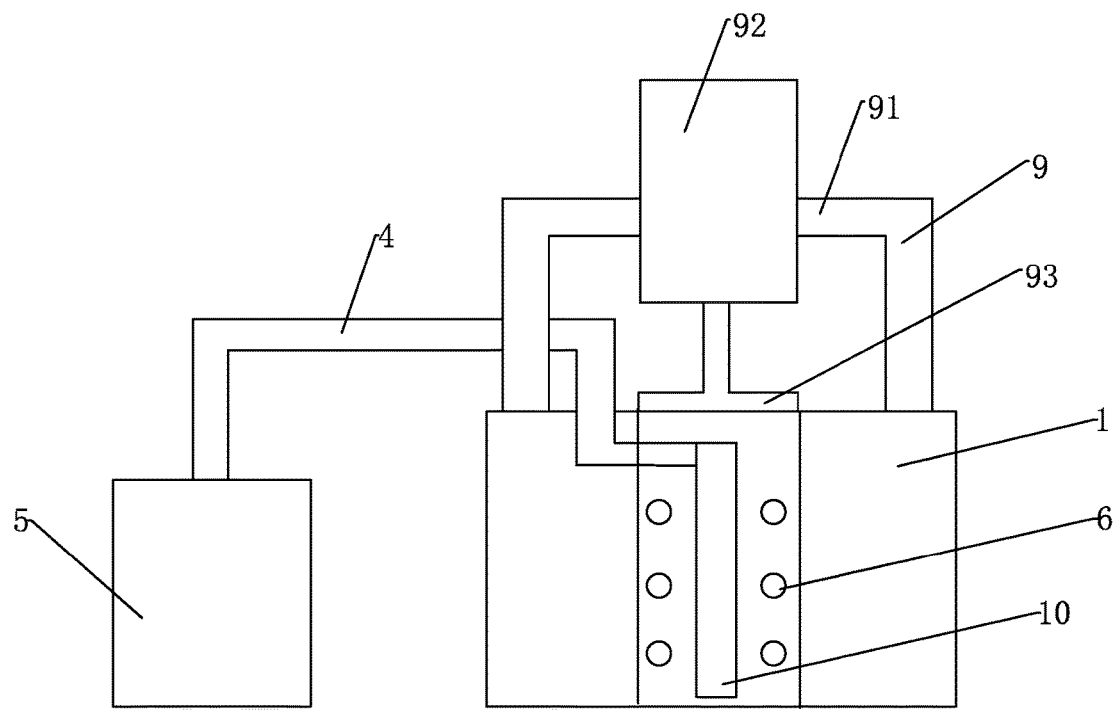
FIG. 1 is a structural diagram of a box, a preloading device and a vacuum pump in a device used in laboratories to measure horizontal displacement of soil around a region to be treated by vacuum preloading according to the present invention.
Figure 2:
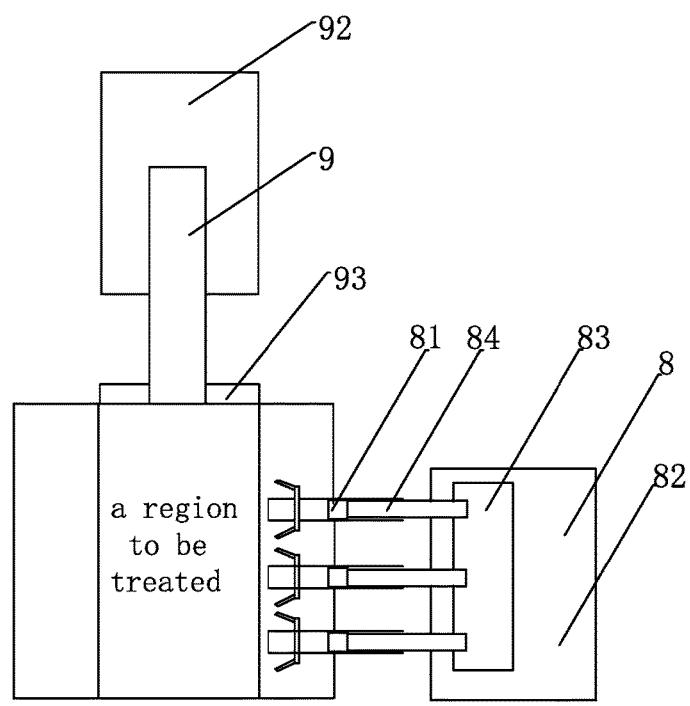
FIG. 2 is a structural diagram when the box of FIG. 1 is equipped with a sensing instrument.
Figure 3:
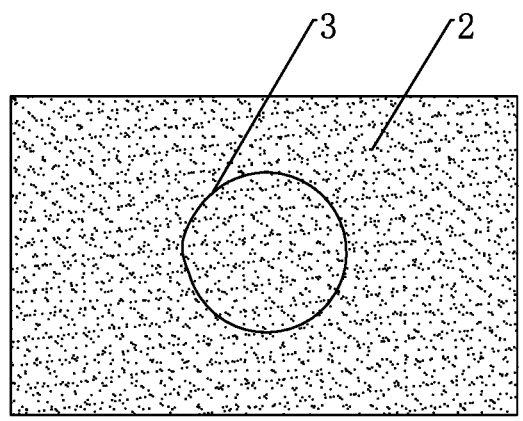
FIG. 3 is a top view of the box.

Referring to FIG. 1 and FIG. 2, the present invention provides a device used in laboratories to measure horizontal displacement of soil around a region to be treated by vacuum preloading, including a box 1. Dredger fill 2 is injected into the box 1. A vertical plastic drainage board 10 and a vacuum pumping tube 4 are buried within soil in the region to be treated, with the vacuum pumping tube 4 being provided with a vacuum degree detector, a lower end of the vacuum pumping tube 4 being connected to the plastic drainage board 10 and an upper end thereof being connected to a vacuum pump 5. A seal membrane 3 is provided in the dredger fill 2, with the seal membrane 3 covering or wrapping soil in the region to be treated so that the interior of the seal membrane 3 is kept sealed. There are two ways to arrange the seal membranes 3: first, the seal membrane 3 is made of PVC and covers soil in the region to be treated, and an end of the seal membrane 3 is buried so that a negative pressure is formed below the seal membrane 3 to increase the effective stress of the foundation; and second, the seal membrane 3 wraps the dredger fill 2 to be treated, and the vacuum pumping tube 4 is connected to the plastic drainage board 10 and to the vacuum pump 5 by passing through the seal membrane 3. A loading device is provided above the seal membrane 3 to assist the drainage. Transverse tubes 6 are inserted into a side of the box 1, the transverse tubes 6 being in surrounding dredger fill 2 of the region to be treated. An annular sensing source 7 which is movable along the transverse tubes 6 together with soil is sleeved on the transverse tubes 6. Each of the transverse tubes 6 is provided with a sensing instrument 8, and the sensing instrument 8 is connected with a sensor 81 which can be inserted into the transverse tube 6. When the sensor 81 reaches the sensing source 7, an audible alarm may be sent, or directly, position data may be recorded and displayed by computer systems such as the programmable logic controller. In this embodiment, a number of transverse tubes 6 are distributed in the height direction of the box 1.

Figure 4:
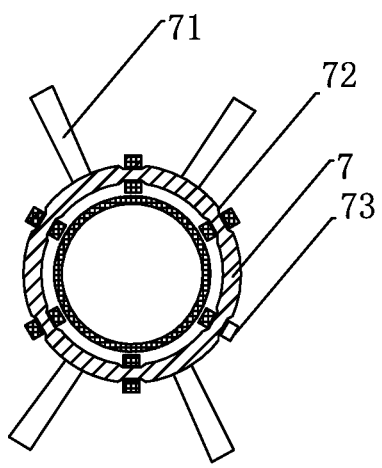
FIG. 4 is a structural diagram of transverse tubes having an annular sensing source sleeved thereon, in the device used in laboratories to measure horizontal displacement of soil around a region to be treated by vacuum preloading according to the present invention.

Referring to FIG. 4, to enable the annular sensing source 7 to move more flexibly, a foot 71 is extended obliquely and outward from the annular sensing source 7, by which soil drives the annular sensing source 7 to move; and at least three recesses 72 with a smaller diameter are evenly distributed on an annular body of the annular sensing source 7, and a roller 73 is sleeved on each of the recesses 72.

Referring to FIG. 2, for the purpose of automatic measurement, the sensing instrument 8 comprises a sensing instrument body 82 on which a telescopic driving device 83 is provided; each of the transverse tubes 6 is provided with a telescopic rod 84 which is driven by the telescopic driving device 85; the sensor 81 is arranged at an end of the telescopic rod 84; the telescopic driving device 83 and a sensing device of the sensing instrument 8 are connected to a programmable logic controller which is programmed to send a signal to the telescopic driving device at regular intervals to urge the telescopic driving device to drive the telescopic rod 84 and the sensor 81 to do one telescopic motion forward or backward; and during the telescopic motion, the programmable logic controller records the position of the annular sensing source 7 whenever sensed by each sensor 81.

Referring to FIG. 1, to automatically apply loads more flexibly, the loading device comprises a support 9; a hydraulic device 92 is provided on a cross bar 91 of the support 9; a chassis 93 is extended downward from the hydraulic device 92 and resisted against the seal membrane 3 to form a positive pressure. The hydraulic device 92 is connected to the programmable logic controller.

Referring to FIG. 1 and FIG. 2, the present invention further provides a method for measuring horizontal displacement of soil around a region to be treated by vacuum preloading, by using the device used in laboratories to measure horizontal displacement of soil around a region to be treated by vacuum preloading, comprising the following steps:

A: injecting dredger fill 2 into a box of the device for measuring horizontal displacement of soil around a foundation to be treated by vacuum preloading in indoor tests; burying a vertical drainage board 10 and a vacuum pumping tube 4 within soil in the region to be treated, with a lower end of the vacuum pumping tube 4 being connected to the plastic drainage board 10 and an upper end thereof being connected to a vacuum pump 5, a seal membrane 3 covering or wrapping soil in the region to be treated, an end of the seal membrane being buried so that the interior of the seal membrane is kept sealed; then activating the vacuum pump so that a negative pressure is formed below the seal membrane 3; and loading above the seal membrane 3 by using the loading device to form a positive pressure;

B: inserting the sensor 81 into the transverse tubes 6 at regular intervals and recording the sensed position of the annular sensing source 7; and C: calculating the amount of displacement of the annular sensing source 7 according to the data of the position of the annular sensing source 7 sensed by the sensor 81, detecting and obtaining the vacuum degree data by using a vacuum degree detector, calculating and loading the data by the loading device, and establishing a test model together with the amount of displacement, the loading force data, the vacuum degree data and the time span.

The invention claimed is:

1. A device used in laboratories to measure horizontal displacement of soil around a region to be treated by vacuum preloading, comprising:

a box with a top surface, a bottom surface and a peripheral side surface filled with soil, the soil being divided into a central soil region to be treated by vacuum preloading and a peripheral soil region surrounding the central soil region;

a vertical drainage board and a vacuum pumping tube being buried within the soil in the central soil region, a lower end of the vacuum pumping tube being connected to the vertical drainage board and an upper end thereof being connected to a vacuum pump;

a sealing membrane above a top soil surface of the central soil region;

a loading device above the sealing membrane to assist drainage;

transverse tubes horizontally inserted into and fixed relative to the peripheral side surface of the box, a part of the transverse tubes being in the peripheral soil region;

an annular sensing source which moves with the soil of the peripheral soil region and which is movable along the transverse tubes and is sleeved on the transverse tubes, wherein a foot is extended obliquely and outwardly from the annular sensing source, by which the soil of the peripheral soil region drives the annular sensing source to move when the soil of the peripheral soil region moves due to the vacuum preloading of the central soil region; and;

a position sensing instrument with a sensing head, wherein the sensing head is adapted to be inserted into the transverse tube from outside of the box, so that when the sensing head reaches position of the annular sensing source along the transverse tubes, an alarm signal is sent, and in this way, different positions of the annular sensing source along the transverse tubes at different moments of time are determined and horizontal displacement of the soil in the peripheral soil region is calculated.

2. The device used in laboratories to measure horizontal displacement of soil around a region to be treated by vacuum preloading according to claim 1, characterized in that a number of transverse tubes are distributed in height direction of the box.

3. The device used in laboratories to measure horizontal displacement of soil around a region to be treated by vacuum preloading according to claim 2, characterized in that the position sensing instrument further comprises:
- a sensing instrument body;
- a telescopic driving device in connection with the sensing instrument body;
- a telescopic rod in connection with and driven by the telescopic driving device, and the sensing head being arranged at an end of the telescopic rod;
- a programmable logic controller to which the telescopic driving device and the sensing head of the position sensing instrument are operably connected, wherein the programmable logic controller is programmed to send a signal to the telescopic driving device at regular intervals to urge the telescopic driving device to drive the telescopic rod and the sensing head to do one telescopic motion forward or backward; and during the telescopic motion, the programmable logic controller records the position of the annular sensing source whenever sensed by each sensing head.

4. The device used in laboratories to measure horizontal displacement of soil around a region to be treated by vacuum preloading according to claim 2, characterized in that the loading device comprises a support; a hydraulic device is provided on a cross bar of the support; a chassis is extended downward from the hydraulic device and resisted against the sealing membrane to form a positive pressure.

5. The device used in laboratories to measure horizontal displacement of soil around a region to be treated by vacuum preloading according to claim 1, characterized in that at least three recesses with a smaller diameter are evenly distributed on an annular body of the annular sensing source, and a roller is sleeved on each of the recesses.

6. The device used in laboratories to measure horizontal displacement of soil around a region to be treated by vacuum preloading according to claim 5, characterized in that the position sensing instrument further comprises:
- a sensing instrument body;
- a telescopic driving device in connection with the sensing instrument body;
- a telescopic rod in connection with and driven by the telescopic driving device, and the sensing head being arranged at an end of the telescopic rod;
- a programmable logic controller to which the telescopic driving device and the sensing head of the position sensing instrument are operably connected, wherein the programmable logic controller is programmed to send a signal to the telescopic driving device at regular intervals to urge the telescopic driving device to drive the telescopic rod and the sensing head to do one telescopic motion forward or backward; and during the telescopic motion, the programmable logic controller records the position of the annular sensing source whenever sensed by each sensing head.

7. The device used in laboratories to measure horizontal displacement of soil around a region to be treated by vacuum preloading according to claim 6, characterized in that the loading device comprises a support; a hydraulic device is provided on a cross bar of the support; a chassis is extended downward from the hydraulic device and resisted against the sealing membrane to form a positive pressure; the hydraulic device connects with the programmable logic controller.

8. The device used in laboratories to measure horizontal displacement of soil around a region to be treated by vacuum preloading according to claim 5, characterized in that the loading device comprises a support; a hydraulic device is provided on a cross bar of the support; a chassis is extended downward from the hydraulic device and resisted against the sealing membrane to form a positive pressure.

9. The device used in laboratories to measure horizontal displacement of soil around a region to be treated by vacuum preloading according to claim 1, characterized in that the position sensing instrument further comprises:
- a sensing instrument body;
- a telescopic driving device in connection with the sensing instrument body;
- a telescopic rod in connection with and driven by the telescopic driving device, and the sensing head being arranged at an end of the telescopic rod;
- a programmable logic controller to which the telescopic driving device and the sensing head of the position sensing instrument are operably connected, wherein the programmable logic controller is programmed to send a signal to the telescopic driving device at regular intervals to urge the telescopic driving device to drive the telescopic rod and the sensing head to do one telescopic motion forward or backward; and during the telescopic motion, the programmable logic controller records the position of the annular sensing source whenever sensed by each sensing head.

10. The device used in laboratories to measure horizontal displacement of soil around a region to be treated by vacuum preloading according to claim 1, characterized in that the loading device comprises a support; a hydraulic device is provided on a cross bar of the support; a chassis is extended downward from the hydraulic device and resisted against the sealing membrane to form a positive pressure.

* * * * *